United States Patent [19]

Petersen

[11] Patent Number: 5,440,935
[45] Date of Patent: Aug. 15, 1995

[54] APPARATUS FOR COMBINING TRANSDUCER OUTPUT SIGNALS

[75] Inventor: Niel R. Petersen, Minnetonka, Minn.

[73] Assignee: MTS Systems Corporation, Eden Prairie, Minn.

[21] Appl. No.: 32,990

[22] Filed: Mar. 18, 1993

[51] Int. Cl.6 ............................................. G01P 15/00
[52] U.S. Cl. ........................................ 73/765; 73/489; 73/900
[58] Field of Search ............... 73/489, 517 R, 763, 73/765, 767, 769, 772, 781, 432.1, 900

[56] References Cited

U.S. PATENT DOCUMENTS

| | | | |
|---|---|---|---|
| 2,998,090 | 8/1961 | Watson | 73/765 |
| 3,161,821 | 12/1964 | Price et al. | 73/765 |
| 3,568,044 | 3/1971 | Elazar | 73/765 |
| 3,569,707 | 3/1971 | Binder et al. | 73/765 |
| 3,572,109 | 3/1971 | Yerman | 73/765 |
| 3,582,690 | 6/1971 | Yerman | 73/765 |
| 3,775,679 | 11/1973 | Abbe | 324/61 R |
| 3,791,204 | 2/1974 | List et al. | 73/772 |
| 3,847,017 | 11/1974 | Watts | 73/765 |
| 4,081,744 | 3/1978 | Ray | 324/63 |
| 4,146,875 | 3/1979 | Beatson et al. | 73/781 |
| 4,213,348 | 7/1980 | Reinertson et al. | 73/765 |
| 4,282,753 | 8/1981 | Davidson | 73/342 |
| 4,309,653 | 1/1982 | Stack et al. | 73/765 |
| 4,326,171 | 4/1982 | Shaw et al. | 330/256 |
| 4,414,852 | 11/1983 | McNeill | 73/765 |
| 4,465,075 | 8/1984 | Swartz | 128/672 |
| 4,572,001 | 2/1986 | Saimoto et al. | 73/765 |
| 4,701,689 | 10/1987 | Yuan et al. | 322/19 |
| 4,795,965 | 1/1989 | Dooley | 324/61 R |
| 4,800,513 | 1/1989 | Deutsch | 73/765 |
| 4,800,749 | 1/1989 | Merrick | 73/4 R |
| 5,182,519 | 1/1993 | Suzuki | 73/765 |
| 5,367,910 | 11/1994 | Woodward | 73/861 |

OTHER PUBLICATIONS

Specification sheet of ICSENSORS Accelerometer Model 3145.
Specification sheel of ICSENSORS Accelerometer Models 3021 and 3026.
Article entitled "Potential Errors in Dynamic Mechanical Analysis Testing and Possible Solutions" by William C. Diamond et al., *Rubber World*, Jan. 1991, pp. 22–25.
Article entitled "Tiny Silicon Devices sense Direction in Everything from Autos to Shoes" by Dana L. Gardner, *Design News*, Jul. 17, 1989, pp. 55–57.

*Primary Examiner*—Richard E. Chilcot, Jr.
*Assistant Examiner*—George M. Dombroske
*Attorney, Agent, or Firm*—Westman, Champlin & Kelly

[57] ABSTRACT

A sensing apparatus for sensing at least two physical quantities is disclosed. The sensing apparatus includes a first transducer that provides a first output signal proportional to a first measured quantity represented and a second transducer that provides a second output signal proportional to a second measured quantity. An excitation regulator device is connected to the first transducer and the second transducer. The excitation regulator device provides an excitation signal to the second transducer so that the second transducer output signal is referenced to the first transducer output signal in order to obtain a resultant output signal which is a combination of the first and second output signals.

21 Claims, 4 Drawing Sheets

APPARATUS FOR COMBINING TRANSDUCER OUTPUT SIGNALS

BACKGROUND OF THE INVENTION

The present invention relates to an apparatus used to combine signals representing at least two physical quantities and provide a single resultant signal. More particularly, the present invention relates to a an apparatus for combining a first output signal proportional to a first measured quantity represented by a difference in signals from a first pair of output terminals with a second output signal proportional to a second quantity represented by a difference in signals from a second pair of output terminals.

Figure 1:
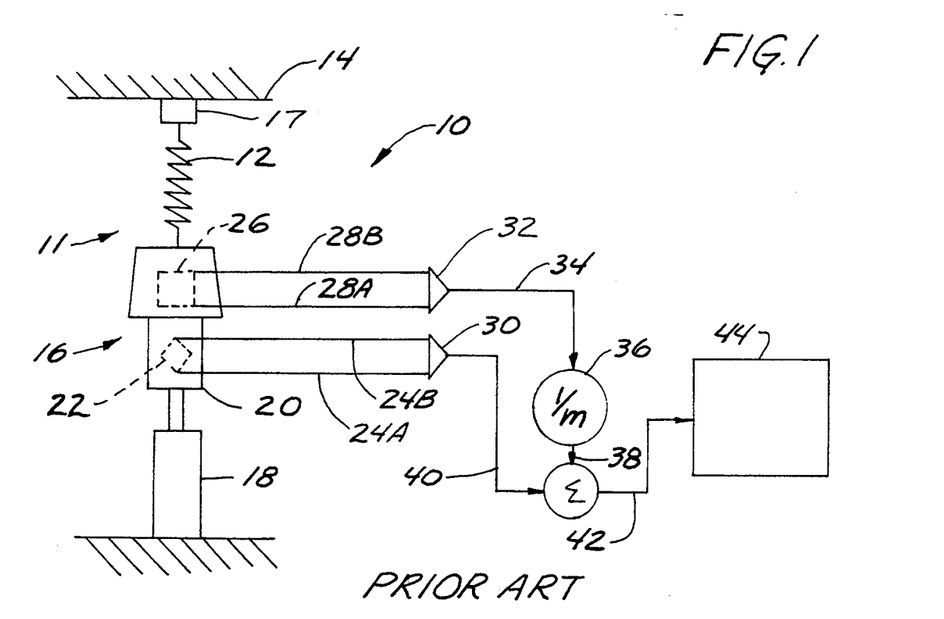
FIG. 1 is a schematic representation of a prior art force measuring system.

Transducers for measuring physical parameters are well known. For example, load cells are commonly used when determining rotational loads and axial loads about or along a reference axis. FIG. 1, discussed further below, schematically illustrates a test apparatus used for imparting forces to a test system that includes, as used herein, a test specimen, a reaction structure and a specimen attachment fixture.

Since it is desirable to obtain the force applied to the test specimen, acceleration compensation is provided to the test system to remove or delete the force required to accelerate the specimen attachment fixture. Commonly, the acceleration signal is transmitted using signal lines that are isolated from the signal lines used to transmit a signal proportional to the force applied by the test system. At a remote location away from the test system the acceleration signal is combined with the force signal to remove the force required to accelerate the attachment fixture and thereby obtain a force signal more representative of the actual force applied to the test specimen.

SUMMARY OF THE INVENTION

A sensing apparatus for sensing at least two physical quantities is disclosed. The sensing apparatus includes a first transducer that provides a first output signal proportional to a first measured quantity represented by a difference in signals from a pair of first output terminals and a second transducer that provides a second output signal proportional to a second measured quantity represented by a difference in signals from a pair of second output terminals, the second transducer having an excitation reference terminal. An excitation regulator device is connected to one of the first output terminals and one of the second output terminals and has an output connected to the excitation reference terminal. The excitation regulator device provides an excitation signal to the second transducer so that the second transducer output signal is referenced to the first transducer output signal to obtain a resultant output signal across two of the output terminals proportional to a combination of the first and second output signals.

The present invention is suited for combining or summing the output signals from like transducers, for instance, summing two linear acceleration signals to provide a signal proportional to angular acceleration. As stated above, the excitation regulator device has an input terminal connected to each of the accelerometers with an output terminal connected to an excitation reference terminal typically, the common terminal of the second transducer. A resultant output signal obtained across the output terminal of the first accelerometer connected to the excitation regulator device and the remaining terminal of the second accelerometer is then proportional to the angular acceleration of the attached fixture.

In another embodiment, the present invention combines output signals from different parameter sensing transducers. For instance, embodied as a compensating force measuring circuit, the present invention measures the force applied to a test specimen in a test system wherein the test system includes the test specimen, a reaction structure and a specimen attachment fixture. The force measuring circuit includes a force sensing device to measure force applied to the test system. The force sensing device provides a force output signal comprising the difference in signals at first and second force output terminals, which difference is proportional to a force applied to the test system. The force measuring circuit further includes a parameter sensing device for measuring a parameter of the test system. The parameter sensing device provides a parameter output signal comprising the difference in signals at first and second parameter output terminals, which difference is proportional to the measured parameter of the test system. An excitation regulator device is connected as described above between the force sensing device and the parameter sensing device to regulate excitation of the parameter sensing device. A circuit connects the second parameter output terminal to the second force output terminal to modify the force output signal and thereby obtain a force output signal more representative of the actual force applied to the test specimen.

In a more specific embodiment, the parameter sensing device is an accelerometer that measures acceleration of the test system, in particular, the specimen attachment fixture for the test specimen. The accelerometer provides an output signal comprising the difference in signals at the first and second accelerometer output terminals, which difference is proportional to the acceleration of the fixture.

The excitation regulator device and a resistor connect the accelerometer to the force sensing device. The resistor has a resistance value that is approximately inversely proportional to the mass of the specimen attachment fixture so that a signal proportional to the force necessary to accelerate the specimen attachment fixture is obtained This force signal is combined with the force signal obtained from the force sensing device to obtain a resultant force signal therefrom that is more representative of the actual force applied to the test specimen. By combining the accelerometer signal with the force signal at the test system, isolated signal lines for the accelerometer and the force sensing device can be eliminated with only a single pair of signal lines being used to provide the desired force signal of the test specimen.

In a further preferred embodiment, excitation of the accelerometer and the excitation regulator device, which is preferably an operational amplifier, are provided from the excitation terminals of the force sensing device. As such, elimination of separate excitation lines to the accelerometer reduces wiring costs and improves reliability and efficiency of the testing apparatus.

The present invention can be adapted to measure other physical parameters of the test system. For instance, two accelerometers can be used to measure the torque necessary to rotate a specimen attachment fixture about a given axis. By combining this torque signal with a signal proportional to the overall torque necessary to rotate the specimen attachment fixture and the test specimen, a torque signal that is more representative of the actual torque applied to the test specimen can be obtained.

Other applications include a testing apparatus wherein the test specimen is subjected to surrounding pressures to simulate selected environmental conditions. Since load cells used to measure force applied to the test system are affected by changing pressure loads, a signal proportional to pressure can be combined with the force output signal from the load cell to obtain an output signal that compensates for the pressure effects.

DETAILED DESCRIPTION OF THE PREFERRED EMBODIMENTS

Figure 2:
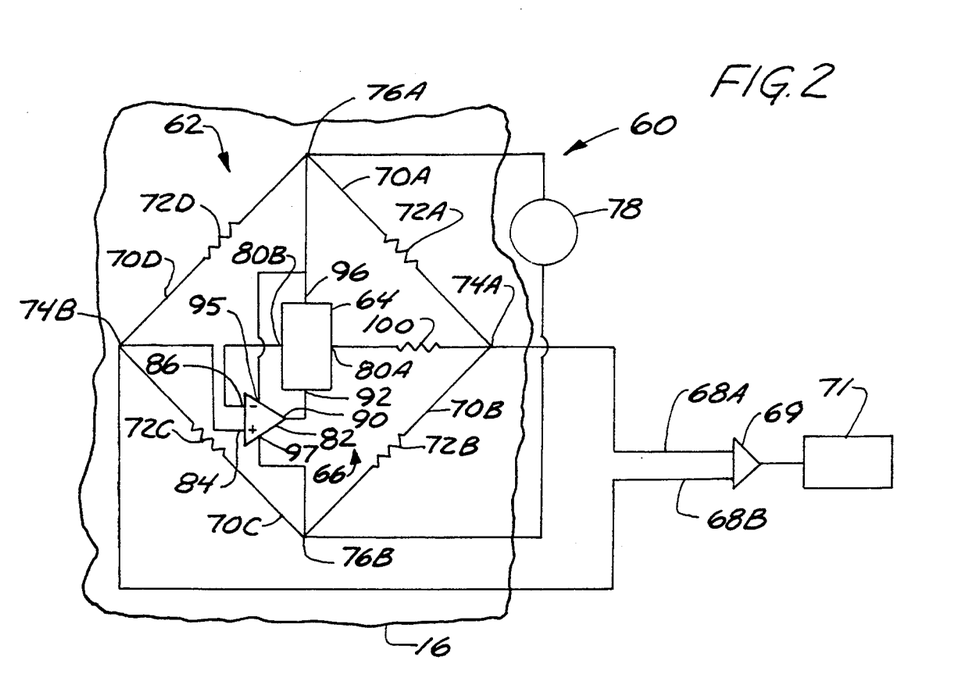
FIG. 2 is a circuit diagram of the present invention.

Embodied as a compensated force measuring circuit, the present invention is illustrated in FIG. 2. However, before discussing that embodiment, a review of a typical prior art compensated force measuring circuit will be helpful. FIG. 1 schematically illustrates a test apparatus 10 used for imparting forces to a test system 11 that includes, as used herein, a test specimen 12, a specimen attachment fixture 16 and a reaction structure 17. The test specimen 12 is connected at a first end to the reaction structure 17 which in turn is mounted to a stationary mass 14. A second end of the test specimen 12 is connected to the specimen attachment fixture 16. The specimen attachment fixture 16 includes a force measuring load cell indicated generally at 20 that is connected to an actuator device 18. The load cell 20 includes a force measuring circuit commonly comprising a Wheatstone bridge having four branches or legs at least one of which being an active strain gage sensor. The Wheatstone bridge is generally indicated with dotted lines at 22 and provides an output signal proportional to the force applied from the actuator device 18 to the test system 11 comprising the difference in signals present on output lines 24A and 24B.

Since it is desirable to obtain the force applied to the test specimen 12, acceleration compensation is provided to the test system 11 to remove or delete the force required to accelerate the specimen attachment fixture 16. Commonly, an acceleration measuring device or accelerometer indicated with dotted lines at 26 attached to the specimen attachment fixture 16 provides an output signal along output lines 28A and 28B proportional to the acceleration experienced by the specimen attachment fixture 16. Separate signal conditioners 30 and 32 connected to the output lines 24A and 24B, and 28A and 28B, respectively, receive the force output signal and the acceleration output signal, respectively, and condition the signals to remove unwanted noise or interference. An output signal along line 34 from signal conditioner 32 represents the acceleration of the specimen attachment fixture 16. A divider circuit 36 divides the signal on line 34 by a value representing the mass of the specimen attachment fixture. An output signal on line 38 from the divider 36 is then proportional to the force required to accelerate the specimen attachment fixture 16. The signal on line 38 is combined with the signal on line 40, which is proportional to the total force delivered by the actuator device 18. The resulting signal on line 42 is proportional to the force applied to the test specimen 12 and is recorded using conventional devices 44 for subsequent analytical purposes.

A force measuring circuit embodiment of the present invention is illustrated schematically in FIG. 2 at 60. Generally, the force measuring circuit 60 includes a force sensing device 62, herein illustrated as a strain gage bridge circuit, a parameter sensing device 64 such as an accelerometer and a circuit 66 to connect the accelerometer 64 to the strain gage bridge circuit 62. With reference back to FIG. 1, the force measuring circuit 60 is mounted to the specimen attachment fixture 16 and provides an output signal on signal lines 68A and 68B proportional to the force applied to the test specimen 12 by compensating for acceleration of the specimen attachment fixture 16 at the test system 11 rather than at a remote location as taught by the prior art illustrated in FIG. 1. The output signal is provided to a suitable signal conditioner 69 and recorder 71. By compensating at the test system 11, the present invention eliminates the need for separate signal lines for the strain gage load sensor and the acceleration sensor as well as one signal conditioner as used in prior art measurement circuits such as illustrated in FIG. 1.

The strain gage bridge circuit 62 is of conventional design and includes four branches or legs 70A, 70B, 70C and 70D connected in a standard Wheatstone bridge circuit. At least one of the branches comprise a strain gage sensor such as a resistive strain gage sensor herein depicted. Commonly, strain sensors 72A, 72B, 72C and 72D are provided in each of the branches so that opposed branches operate in pairs to provide an output signal across terminals 74A and 74B. Conventionally, excitation is provided to terminals 76A and 76B from a power supply 78.

The accelerometer 64 provides an output signal proportional to acceleration of the specimen attachment fixture 16 illustrated in FIG. 1. As used herein, the accelerometer comprises a silicon micromachined accelerometer such as Model 3145 manufactured by ICSensors of Milpitas Calif. This accelerometer includes amplification, signal conditioning and temperature compensation. Other types of accelerometers such as Models 3021 and 3026, solid state piezo-resistive accelerometers, manufactured by ICSensors of Milpitas Calif. can also be used. Using the latter accelerometers, amplification, signal conditioning and temperature compensation must be included as needed with support circuitry as is conventionally known.

As stated, the accelerometer 64 provides an output signal proportional to the acceleration of the specimen attachment fixture 16 to which it is attached. This output signal is combined with and referenced to the output signal provided by the force bridge circuit 62 to provide an acceleration compensated force signal more representative of the force actually applied to the test specimen shown in FIG. 1. The circuit 66 provides means to reference the accelerometer output signal across terminals 80A and 80B to the force bridge circuit 62. As illustrated, the circuit comprises an excitation regulator device 82 such as an operational amplifier having a noninverting input terminal 84 connected to the terminal 74B of the force bridge circuit 62. An inverting input terminal 86 of the operational amplifier 86 is connected to the reference terminal 80B of the accelerometer 64, the reference terminal 80B being one of the output terminals to obtain the output signal. An output terminal 90 of the operational amplifier is connected to an excitation reference terminal 92 typically, the common terminal of the accelerometer 64. The operational amplifier 82 responds to the inputs to regulate the voltage at the excitation reference terminal 92 so that the accelerometer output signal at the terminal 80B is equal to the output signal provided by the force bridge circuit at the terminal 74B. The accelerometer 64 receives a voltage signal at terminal 96 sufficiently above the voltage at the terminal 92 to maintain proper operation. Excitation of the operational amplifier is provided at terminals 95 and 97, which are connected to an excitation power source. Preferably, as illustrated, excitation is provided from the excitation terminals of the force bridge circuit 62 at terminals 76A and 76B.

As connected, the operational amplifier 82 reflects or references the voltage signal at terminal 74B of the force bridge circuit 62 to the accelerometer 64 at reference terminal 80B since the voltage signal at terminal 86 is for practical purposes equal to the voltage at terminal 84. Referencing of the accelerometer 64 to one of the output signals of the force bridge circuit 62 without loading down the force bridge circuit 62 is due to the high internal input impedance of the operational amplifier 82 at terminal 84.

The circuit 66 further includes a resistor 100 connected to the output terminal 80A of the accelerometer 64 and the output terminal 74A of the force bridge circuit 62. The resistor 100 has a resistance value selected to be approximately inversely proportional to the mass of the specimen attachment fixture. Preferably, the resistor 100 is variable to allow further adjustments for inaccuracies of the accelerometer and different applications to other specimen attachment fixtures. The resistance value of the resistor is given by the following equation:

$$R = R_B \left[ \frac{AF}{EM\gamma} - 1 \right] \text{OHMS}$$

where A represents the scaling factor of the accelerometer (mV/g), F represents force bridge circuit full scale rating (lbs), E represents force bridge circuit excitation voltage (V), M represents mass of the specimen attachment fixture (lbs$_m$), $\gamma$ represents force bridge circuit differential output signal (mV/V) at full scale rating (F), and $R_B$ represents the output impedance of the force bridge circuit (Ohms).

The circuit 66 thus connects the accelerometer 64 to the force bridge circuit 62 such that the accelerometer 64 can be mounted at or near the load cell with acceleration compensation provided thereat, minimizing wiring and components of the testing apparatus.

Figure 3:
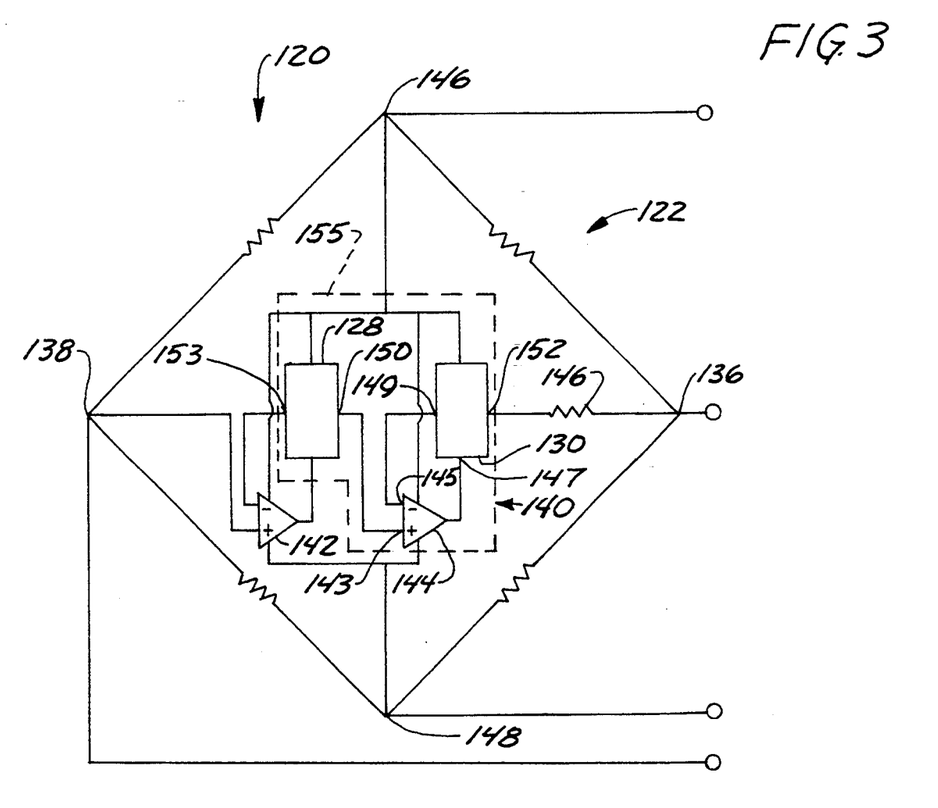
FIG. 3 is a circuit diagram of a second embodiment of the present invention.

FIG. 3 illustrates a second embodiment of the present invention wherein a compensating force measuring circuit 120 provides an output signal proportional to the torque applied to a test specimen by compensating for angular acceleration of the specimen attachment fixture.

Figure 4:
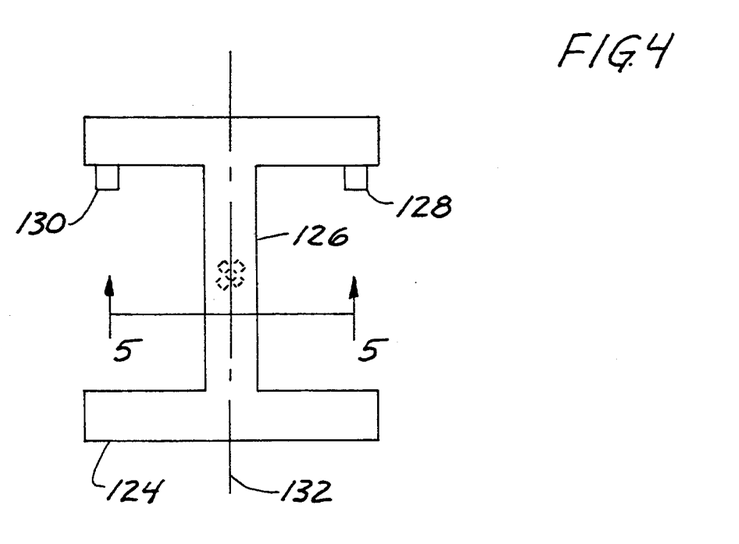
FIG. 4 is a side elevational view of a torque transducer and specimen attachment fixture.
Figure 5:
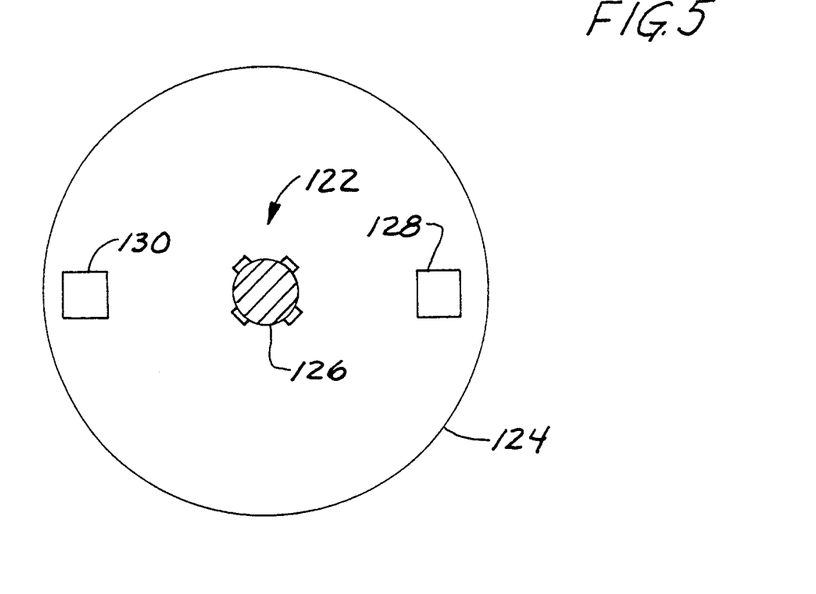
FIG. 5 is a sectional view of the torque transducer taken as on line 5—5 in FIG. 4.

Referring to FIGS. 4 and 5, a torque sensing bridge circuit 122 is conventionally adhered to a specimen attachment fixture 124 such as at center support column 126. Two accelerometers 128 and 130 are mounted to the specimen attachment fixture 124 at a common radius from a central axis 132 180° apart for angular displacement about the central axis 132. As mounted, the accelerometers 128 and 130 together provide an output signal proportional to angular acceleration of the specimen attachment fixture 124 about the central axis 132.

Referring now to FIG. 3 wherein the torque sensing bridge circuit 122 is represented schematically, the accelerometers 128 and 130 are series connected across output terminals 136 and 138 with a circuit 140 including operational amplifiers 142 and 144 and an inertia compensating resistor 146. As illustrated, excitation is provided from the excitation terminals 146 and 148 of the torque sensing bridge circuit 122, but can be provided from a separate power source if desired. The operational amplifier 142 is connected to one of the output terminals of the torque sensing bridge circuit to reflect or reference the accelerometer 128 outputs thereto, while isolating the accelerometer 128 from the torque sensing bridge circuit to reduce undesirable loading of the output terminals 136 and 138. In turn, an output terminal 150 of the accelerometer 128 is series connected to the accelerometer 130 through the operational amplifier 144, thereby maintaining isolation between the accelerometers 128 and 130, while referencing the accelerometer 130 to the output signal at the terminal 150. An output terminal 152 of the second accelerometer 130 is connected to the inertia compensating resistor 146 with an opposed terminal connected to the output terminal 136 of the torque sensing bridge circuit 122. The above-described series connected accelerometer circuit using a single variable resistor assumes essentially identical characteristics of the accelerometers positioned at an equal distances from the central axis. The resistance value of the resistor is given by the following equation:

$$R = R_B \left[ \frac{AT}{EI\gamma} - 1 \right] \text{OHMS}$$

where A represents the scaling factor of the accelerometers (mV/rad/sec$^2$), T represents the bridge circuit full scale torque rating (in.lbs), E represents bridge circuit excitation voltage (V), I represents the moment of inertia of the specimen attachment fixture (in.lbs$_m$.sec$^2$), $\gamma$, represents the bridge circuit differential output signal (mV/V) at full scale torque rating (T), and $R_B$ represents the output impedance of the bridge circuit (Ohms).

The series connected circuit of accelerometers 128 and 130 further illustrates another embodiment of the present invention. Each of the accelerometers 128 and 130 provides an output signal proportional to acceleration of the specimen attachment fixture 124. Similar to the embodiment of FIG. 2, the operational amplifier 144 is connected to one of the outputs for each of the accelerometers 128 and 130 at a non-inverting input 143 and an inverting input 145, respectively. The operational amplifier 144 regulates the voltage at an excitation reference terminal 147 of the accelerometer 130 so that the accelerometer output signal at the terminal 149 is equal to the output signal provided by the accelerometer 128 at the terminal 150. A resultant output signal, being a combination of the signals from each of the accelerometers 128 and 130, is taken across a terminal 153 of the accelerometer 128 and the terminal 152 of the accelerometer 130. Denoting an angular acceleration sensing circuit 155 as the accelerometers 128 and 130 with the operational amplifier 144, it is apparent that the circuit 155 is connected to the torque sensing bridge circuit 122 with the operational amplifier 142 and the compensating resistor 146 similarly to the embodiment of FIG. 2.

Figure 6:
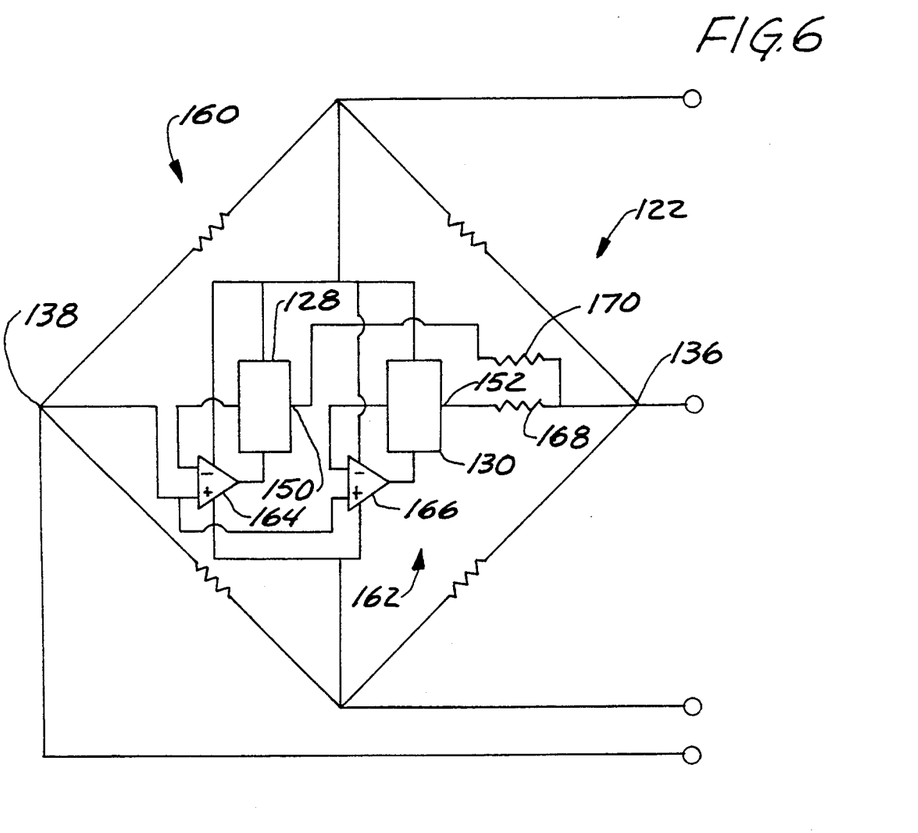
FIG. 6 is a circuit diagram of a third embodiment of the present invention.

FIG. 6 illustrates a second angular acceleration compensated torque bridge circuit 160 for the specimen attachment fixture 124 of FIGS. 4 and 5. The torque compensated force bridge circuit 160 differs from the circuit 120 illustrated in FIG. 3 in that each accelerometer 128 and 130 are referenced to the terminal 138 by a circuit 162. As illustrated, the circuit 162 includes operational amplifiers 164 and 166 and inertia compensating resistors 168 and 170. The operational amplifiers 164 and 166 reflect the voltage at the terminal 138 to accelerometers 128 and 130, respectively, in the manner described above, while maintaining isolation between the terminals 136 and 138. The inertia compensating resistors 168 and 170 are connected to output terminals 150 and 152, respectively and are adjusted to a value using known principles to provide a signal proportional to the torque applied to rotate the specimen attachment fixture 124.

Figure 7:
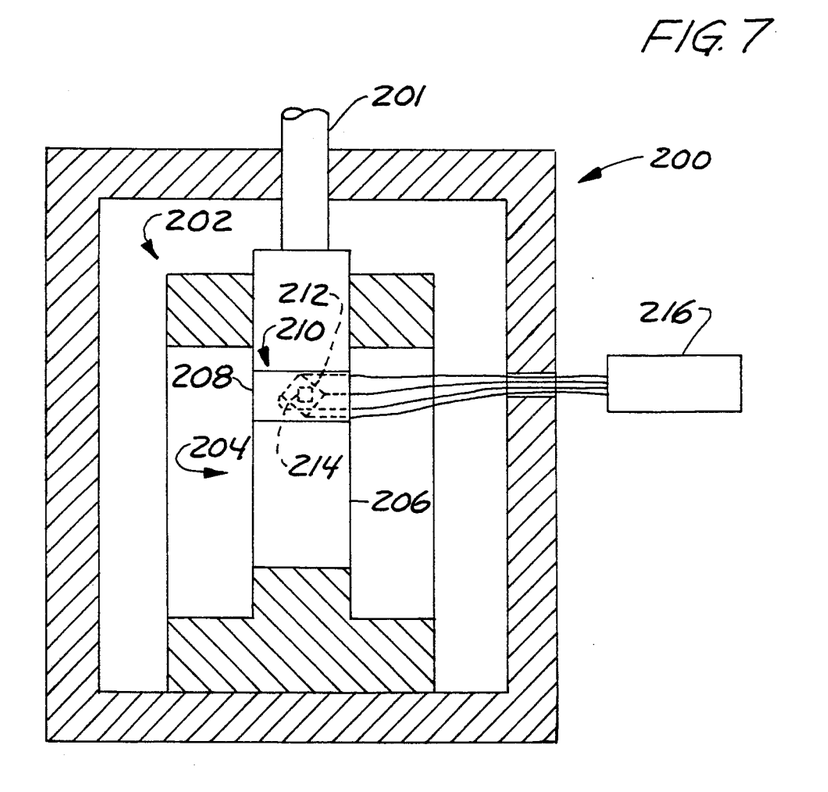
FIG. 7 is a schematic representation of a test apparatus.

The present invention can be adapted to measure and compensate for other physical parameters of a test system. Referring to FIG. 7, an environmental chamber 200 encloses a testing apparatus 202 to vary the surrounding pressure upon a test system 204 placed therein. At a selected pressure within the environmental chamber 200, an actuator, not shown, applies force to the test system 204 through a connecting rod 201. A pressure compensated force bridge circuit 210, having a force bridge circuit 212 and a pressure sensor 214, both schematically illustrated with dotted lines, provides a force signal to a test controller 216 more representative of the true force applied to the test specimen 206 by compensating for pressure effects.

Figure 8:
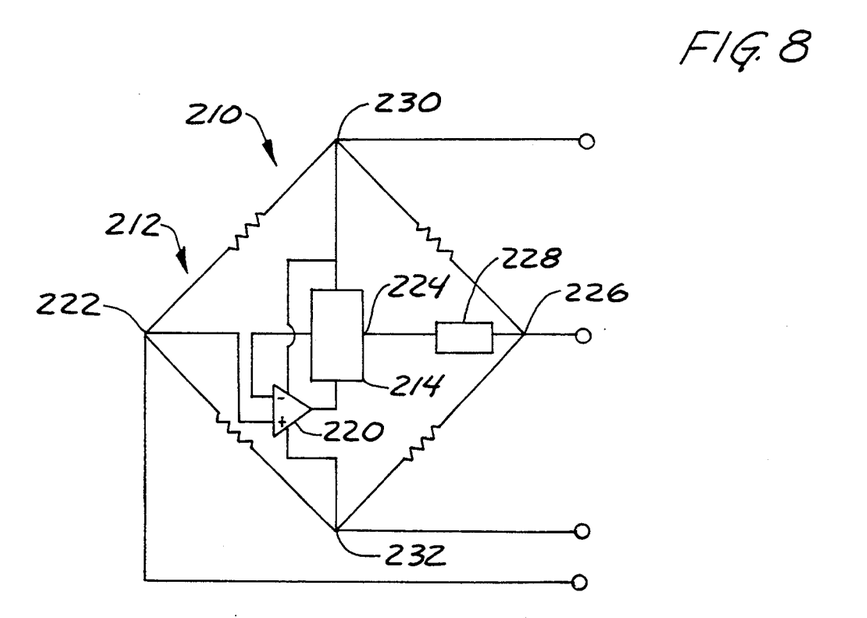
FIG. 8 is a circuit diagram of a fourth embodiment of the present invention.

Referring to FIG. 8, the pressure compensated force bridge circuit 210 includes an operational amplifier 220 to connect the pressure sensor 214 to the force bridge circuit 212. In the manner described above, the operational amplifier 220 references the pressure sensor 214 to the output voltage signal at a terminal 222. An output terminal 224 of the pressure sensor 214 is connected to a suitable scaling circuit 228, if required, to scale the output signal from the pressure sensor 214 to provide proper compensation across the output terminals 222 and 226. As with the embodiments described above, excitation of the pressure sensor 214 and operational amplifier 220 is preferably provided from excitation terminals 230 and 232 of the force bridge circuit 212 to minimize signal conditioning components and test apparatus wiring.

In summary, the present invention provides an apparatus that combines output signals from at least two transducers to reduce components and wiring costs. The present invention is well suited for testing apparatuses used to analyze test specimens, but is also equally applicable to systems wherein transducers are used to sense physical parameters for control purposes.

Although the present invention has been described with reference to preferred embodiments, workers skilled in the art will recognize that changes may be made in form and detail without departing from the spirit and scope of the invention.

What is claimed is:

1. A sensing apparatus for sensing at least two physical quantities, the sensing apparatus comprising:
   a first transducer providing a first output signal proportional to a first measured quantity represented by a difference in signals from a pair of first output terminals;
   a second transducer providing a second output signal proportional to a second measured quantity represented by a difference in signals from a pair of second output terminals, the second transducer having an excitation reference terminal; and
   an excitation regulator device having an output connected to the excitation reference terminal and a first input connected to one of the first output terminals and a second input connected to one of the second output terminals, the excitation regulator device providing an excitation signal to the second transducer so that said one of the second output terminals to obtain a resultant output signal across two of the output terminals proportional to a combustion of the first and second output signals.

2. The sensing apparatus of claim 1 wherein the first transducer is a force transducer connected to a system an attachment fixture, the force transducer measuring force imparted to the system.

3. The sensing apparatus of claim 2 wherein the force transducer comprises a Wheatstone bridge having a strain sensing device.

4. The sensing apparatus of claim 2 and further including a chamber, and wherein the second transducer comprises a pressure transducer for measuring pressure within the chamber.

5. The sensing apparatus of claim 2 wherein the second transducer comprises an accelerometer to measure acceleration of the attachment fixture.

6. The sensing apparatus of claim 2 wherein the force transducer measures torque applied to the system, and wherein the second transducer comprises an accelerometer measuring angular acceleration of the attachment fixture.

7. The sensing apparatus of claim 1 wherein the resultant output signal is obtained from said one of the first output terminals and an output terminal of the second transducer opposite said one of the second output terminals.

8. The sensing apparatus of claim 1 and further including means for connecting an output terminal of the first output terminals opposite said one of the first output terminals to an output terminal of the second transducer opposite said one of the second output terminals, the resultant output signal being obtained from the first output terminals and being a modified signal of the first output signal.

9. The sensing apparatus of claim 8 wherein the first transducer is a force transducer connected to a system including an attachment fixture, the force transducer measuring force imparted to the system; and wherein the second transducer is an accelerometer measuring acceleration of the attachment fixture; and wherein the means for connecting comprises a resistor having a value to compensate for the mass of the attachment fixture.

10. The sensing apparatus of claim 1 wherein the first measured quantity and the second measured quantity are the same.

11. The sensing apparatus of claim 10 wherein the first transducer comprises an accelerometer and the second transducer comprises a second accelerometer.

12. The sensing apparatus of claim 1 wherein the excitation regulator device comprises an operational amplifier.

13. The sensing apparatus of claim 1 wherein the second transducer includes a second excitation terminal and the first transducer includes a pair of excitation terminals, the second excitation terminal of the second transducer being connected to one of the pair of excitation terminals of the first transducer, the excitation regulator device having power terminals connected to the pair of excitation terminals of the first transducer.

14. The sensing apparatus of claim 1 wherein the first measured quantity is different than the second measured quantity.

15. A sensing apparatus for sensing at least two physical quantities, the sensing apparatus comprising:
- a first transducer comprising a sensing bridge providing a first output signal proportional to a first measured quantity represented by a difference in signals from a first bridge output terminal and a second bridge output terminal;
- a second transducer providing a second output signal proportional to a second measured quantity represented by a difference in signals from a pair of second output terminals, the second transducer having a pair of excitation terminals;
- an excitation regulator device having an output connected to one of the excitation terminals and a first input connected to the first bridge output terminal and a second input connected to one of the second output terminals, the excitation regulator device providing an excitation signal to the second transducer so that said one of the second output terminals is equal to the first bridge output terminal; and
- coupling means for coupling the second bridge output terminal to an output terminal of the second transducer opposite said one of the second output terminals, a resultant output signal being obtained from the first and second bridge output terminals and being a modified signal of the first output signal.

16. The sensing apparatus of claim 15 wherein the excitation regulator device comprises an operational amplifier.

17. The sensing apparatus of claim 16 wherein the coupling means comprises a resistor.

18. A force measuring circuit for measuring force applied to a test specimen in a test system, the test system including the test specimen and a specimen attachment fixture for supporting the test specimen, the force measuring circuit comprising:
- force sensing means for measuring force applied to the test system, the force sensing means providing a force output to the test system represented by a difference in signals from first and second force output terminals;
- parameter sensing means for measuring a parameter of the test system and providing a parameter output signal from first and second parameter output terminals proportional to the measured parameter of the test system, the parameter sensing means having an excitation reference terminal;
- an excitation regulator device having an output connected to the excitation reference terminal and a first input connected to the first force output terminal and a second input connected to the first parameter output terminal, the excitation regulator device providing an excitation signal to the parameter sensing means so that the first parameter output terminal is equal to the first force output terminal; and
- coupling means for coupling the second force output terminal to the second parameter output terminal, a resultant output signal being obtained from the first and second force output terminals and being a modified signal of the force output signal.

19. The force measuring circuit of claim 18 wherein the excitation regulator device comprises an operational amplifier.

20. The sensing apparatus of claim 19 wherein the coupling means comprises a resistor.

21. A force sensing apparatus for sensing a force applied to a test specimen in a test system, the test system having an attachment fixture for supporting the test specimen, the force sensing apparatus comprising:
- a force transducer operably connected to the test system to sense a force applied to the test system and provide a force output signal proportional to the applied force, the force output signal being a difference in signals from a pair of first output terminals;
- an acceleration transducer operably connected to the test system to sense an acceleration of the attachment fixture and provide an acceleration proportional to the acceleration of the attachment fixture, the acceleration output signal being represented by a difference in signals from a pair of second output terminals, the acceleration transducer having an excitation reference terminal;
- an excitation regulator device having an output connected to the excitation reference terminal and a first input connected to one of the first output terminals and a second input connected to one of the second output terminals, the excitation regulator device providing an excitation signal to the second transducer so that the signal at said one of the second output terminals is equal to the signal at said one of the first output terminals to obtain a resultant output signal across the first output terminals proportional to a combination of the first and second output signals; and
- a resistor having a value to compensate for the mass of the attachment fixture, the resistor being connected to an output terminal of the first output terminals opposite said one of the first output terminals and to an output terminal of the second output terminals opposite said one of the second output terminals, the resultant output signal being obtained from the first output terminals and being a modified signal of the first output signal.

* * * * *

UNITED STATES PATENT AND TRADEMARK OFFICE
CERTIFICATE OF CORRECTION

PATENT NO. : 5,440,935
DATED : August 15, 1995
INVENTOR(S) : Niel R. Petersen

It is certified that error appears in the above-indentified patent and that said Letters Patent is hereby corrected as shown below:

Column 8, line 22, after "terminals" insert --is equal to said one of the first output terminals--.

Column 8, lines 23-24, replace "combustion" with --combination--.

Column 10, line 35, after "acceleration" insert --output signal--.

Signed and Sealed this

Seventh Day of May, 1996

Attest:

BRUCE LEHMAN

Attesting Officer        Commissioner of Patents and Trademarks